US00PP13304P3

(12) United States Plant Patent
Boeder

(10) Patent No.: US PP13,304 P3
(45) Date of Patent: Dec. 3, 2002

(54) CHRYSANTHEMUM PLANT NAMED 'ONYX TIME CREAM'

(75) Inventor: Mark Roland Boeder, West Wittering (GB)

(73) Assignee: Cleangro Limited (GB)

( * ) Notice: Subject to any disclaimer, the term of this patent is extended or adjusted under 35 U.S.C. 154(b) by 50 days.

(21) Appl. No.: 09/768,039

(22) Filed: Jan. 24, 2001

(65) Prior Publication Data

US 2002/0100095 P1 Jul. 25, 2002

(51) Int. Cl.[7] ..... A01H 5/00

(52) U.S. Cl. ..... Plt./289

(58) Field of Search ..... Plt./288, 289

(56) References Cited

U.S. PATENT DOCUMENTS

PP4,585 P 7/1980 Meek et al. ..... Plt./288

*Primary Examiner*—Kent L. Bell
(74) *Attorney, Agent, or Firm*—Howrey Simon Arnold & White, LLP

(57) ABSTRACT

A new variety of Chrysanthemum plant named 'Onyx Time Cream,' having an upright growth habit, a flat capitulum form and medium sized cream-white decorative type inflorescences.

1 Drawing Sheet

LATIN NAME OF THE GENUS AND SPECIES

Botanical classification: *Dendranthema grandiflora.*

VARIETY DENOMINATION

The new Chrysanthemum variety denomination is 'Onyx Time Cream.'

BACKGROUND OF THE INVENTION

The present invention comprises a new and distinct cultivar of Chrysanthemum botanically known as *Dendranthema grandiflora*, and referred to by the cultivar name 'Onyx Time Cream'.

'Onyx Time Cream,' identified as OTC1, was discovered by Mark Boeder in Chichester, West Sussex, United Kingdom, as a whole plant natural mutation in a controlled cultivated planting of the unpatented variety 'Onyx Time.' The new variety 'Onyx Time Cream' has been asexually reproduced by vegetative cuttings in Chichester, West Sussex, United Kingdom and the distinguishing characteristics are retained through successive generations of asexual reproduction.

BRIEF SUMMARY OF THE INVENTION

'Onyx Time Cream' is a pot type of Chrysanthemum plant variety having a flat capitulum form, dark green foliage and medium sized cream-white decorative-type flowers.

Comparison with Parent

Plants of the new Chrysanthemum variety 'Onyx Time Cream' are similar to the parent cultivar 'Onyx Time' in plant habitat and growth rate. In side-by-side comparisons in Chichester, West Sussex, United Kingdom, under commercial practice, plants of the new Chrysanthemum variety 'Onyx Time Cream' produced medium sized cream-white flowers whereas the parent cultivar 'Onyx Time' produced white flowers.

Comparison with Other Varieties

Plants of the new Chrysanthemum variety 'Onyx Time Cream' are dissimilar to the cultivar 'Surf,' U.S. Plant Pat. No. 4,585, in plant habitat and growth rate. In side-by-side comparisons in Chichester, West Sussex, United Kingdom, under commercial practice, plants of the new Chrysanthemum variety 'Onyx Time Cream' differed from plants of the cultivar 'Surf' in at least the following characteristics:

1. The new variety 'Onyx Time Cream' produces cream-white flowers whereas the cultivar 'Surf' produces white flowers.

2. Plants of the new variety 'Onyx Time Cream' have a longer response time than plants of the cultivar 'Surf.'

BRIEF DESCRIPTION OF ILLUSTRATIONS

Typical plant and flowers for the new Chrysanthemum variety 'Onyx Time Cream' are shown in the accompanying scanned image printed from a digital photograph. The colors shown are as true as possible within the usual limits of this kind of illustration.

FIG. 1 is a whole plant view of the new variety 'Onyx Time Cream' grown in a pot. The plant shown in the illustration and described herein is 53 days after the commencement of Short Days.

DETAILED BOTANICAL DESCRIPTION

The following description of the new Chrysanthemum variety 'Onyx Time Cream' is of plants grown in a greenhouse in Chichester, West Susssex, United Kingdom in the month of November 2000. The cultivar has not been observed under all possible environmental conditions. The phenotype may vary significantly with variations in the environment such as temperature, length of day and light intensity, without any variance in genotype. The commercial classification of the new variety is a pot Chrysanthemum.

Plants of the new variety have been grown successfully under temperature conditions averaging about 19° C. at night and about 17° C. to 24° C. during the day under light conditions of about 5,000 to 6,000 foot candles. The plants respond well to the use of growth retardant, such as three B9 treatments at about 2 g/liter. To produce a commercial product the plants may be pinched once with the center bud removed. The typical container size for commercial growth is 1 liter. It has been observed that the shelf life of the new variety is about 21 days with a response time of about 7.5 weeks.

The new variety may be produced as a spray. The following description is with respect to a plant produced as spray pot chrysanthemum. In the descripiton of this new Chrysanthemum variety, color values have been taken from The Royal Horticultural Society Colour Chart (R.H.S.C.C).

Plant

Plant type: Pot.
Habit: Upright.
Height: 17 cm.
Width: 32 cm.
Branching characteristics: Upright spreading.
Length of lateral branches: 15 cm.
Number of breaks from pinch: 4 breaks per pinch.
Stem color: 137B.
Response time: Near 7.5 weeks.
Vigor: Medium.
Shelf life: Near 21 days.
Disease/pest susceptibility/resistance: None observed to date.
Growth retardant type and treatment: 3 applications of 2 gram/liter B9, 2 days, 21 days and 28 days after sticking of unrooted cuttings. The plants were grown for 2 weeks in Long Day conditions (20 hrs. light) and then transferred to Short Day conditions (13 hrs. dark).
Propagation:
*Type.*—Vegetative propagation via stem cuttings.
*Time to rooting.*—14 days with soil temperatures of 18° C.
*Rooting habit.*—After 7 Long Days first roots emerge from root primorida. In 14 Long Days a complete root system is developed.

Foliage

Number of leaves per lateral branch: 9–11.
Compound or single: Single.
Arrangement of leaves: Alternate.
*Shape of leaf.*—Typically 5 lobed, oblong ovate.
*Size of leaf.*—Width (cm): 5.5. Length (cm): 12.
*Leaf apex.*—Mucronate.
*Base.*—Cordate.
*Attachment.*—Petioled.
*Aspect.*—Slight undulating.
*Margin.*—Palmately lobed.
*Surface characteristics.*—Top: pubescent. Bottom: pubescent.
Petiole:
*Color.*—137B.
*Length.*—3.4 cm.
Venation: net, prominent midvein at underside. Color: upper side: 147D. under side: 147C.
Color:
*Mature leaf.*—Upper side: 137A; Under side: 137B.
*Young leaf.*—Upper side: 137B; Under side: 137C.

Inflorescence

Inflorescence type: Decorative.
Number of blossoms per branch: 3–4.
Inflorescence form: Cyme.
*Depth of fully expanded blossoms.*—Near 2 cm.
*Diameter of fully expanded blossoms.*—Near 10.0 cm.
Phyllaries:
*Number.*—19–23.
*Outer surface color.*—137A.
*Inner surface color.*—137C.
*Length.*—1.3 cm.
*Width.*—0.35 cm.
*Texture/appearance.*—Pubescent.
Peduncle:
*Length.*—Terminal: near 5.5 cm; Lateral: 4–15.5 cm.
*Color.*—Near 137B.
*Surface.*—Pubescent.
*Habit.*—Slightly undulating.
*Strength.*—Medium.
Ray florets:
*Form/shape.*—Straight, elliptic.
*Texture/appearance.*—Matte.
*Number per flower.*—200 –220.
*Length.*—0.5–3.5 cm.
*Width.*—0.2–1.0 cm.
*Apex.*—Rounded.
*Base.*—Tapered.
*Margin.*—Entire.
Disc florets:
*Form/shape.*—Cylindric.
*Texture/appearance.*—Shiny.
*Number per flower.*—10–14.
*Length.*—0.2–0.3 cm.
*Width.*—0.05–0.1 cm.
*Diameter of disc.*—Near 0.3 cm.
Fragrance: Faint.
Flower bud (at onset of color):
*Length.*—Near 0.7 cm.
*Diameter.*—Near 1 cm.
*Form/shape.*—Spherical.
General inflorescence color: Creamy white ray florets with green center.
*1. Ray florets, upper side.*—Immature: near 9C. Mature: near 158D. Older/Fading: near 155D.
*2. Ray florets, under side.*—Immature: near 9C. Mature: near 158D. Older/Fading: near 155D.
*3. Disc florets.*—Immature: near 8C. Mature: near 153D. Older/Fading: near 8C.
*4. Bud.*—Near 138A.
Inflorescence progression with age: Flowerbuds open from one side instead of uniform circular opening, slight color fading of ray florets when aging. Center fades from green to yellow.

Reproductive Organs

Ray florets: Pistillate.
*Pistil number.*—5.
*Stigma color.*—Near 6C.
*Stigma shape.*—Forked.
*Style color.*—Near 6C.
*Style length.*—Near 0.6 cm.

Disc florets: Pistillate.

*Pistil number.*—5.

*Stigma color.*—Near 6C.

*Stigma shape.*—Forked.

*Style color.*—Near 6C.

*Style length.*—Near 0.1 cm.

Staminate: None observed to date.

What is claimed is:

1. A new and distinct variety of Chrysanthemum plant named 'Onyx Time Cream' as described and illustrated.

* * * * *

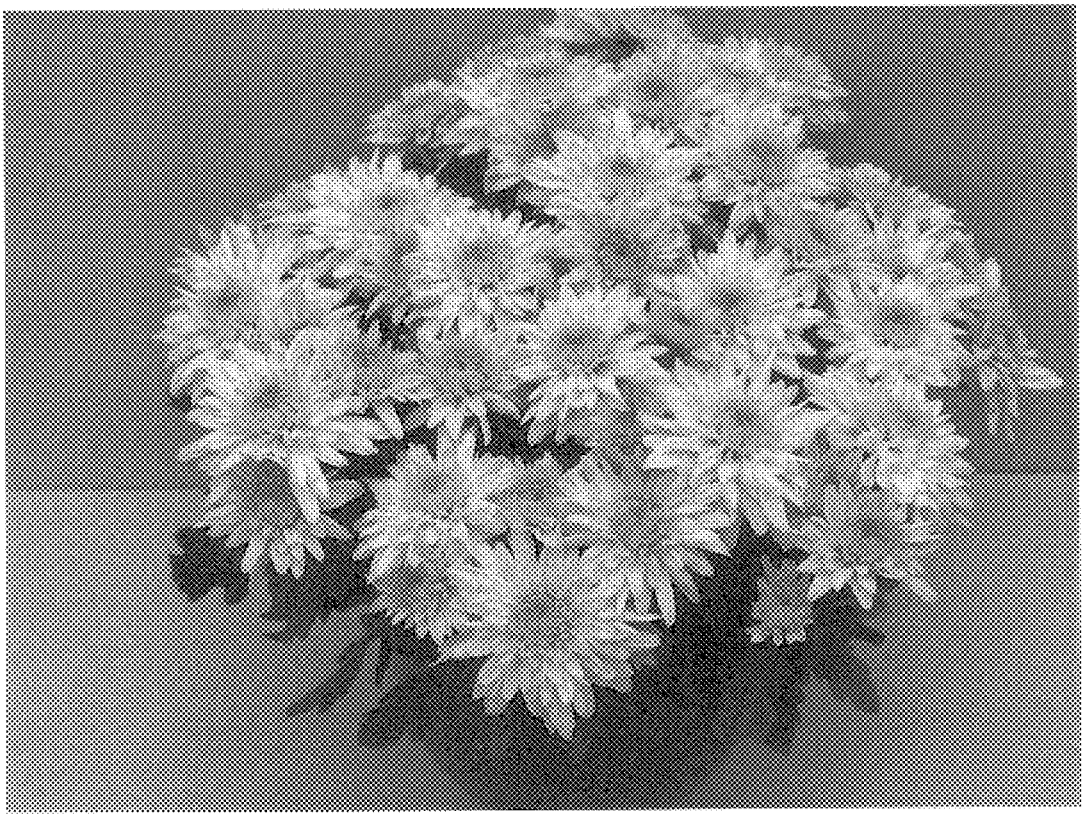

UNITED STATES PATENT AND TRADEMARK OFFICE

CERTIFICATE OF CORRECTION

PATENT NO. : PP 13,304 P3
DATED : December 3, 2002
INVENTOR(S) : Mark Roland Boeder It is certified that error appears in the above-identified patent and that said Letters Patent is hereby corrected as shown below:

Title page,
Item [22], PCT Filed:, change Filed Date, from "January 24, 2001" to
-- January 22, --.

Signed and Sealed this

Second Day of March, 2004

JON W. DUDAS
*Acting Director of the United States Patent and Trademark Office*